(12) United States Patent
Thorens et al.

(10) Patent No.: US 11,974,599 B2
(45) Date of Patent: *May 7, 2024

(54) ELECTRICALLY HEATED SMOKING SYSTEM HAVING A LIQUID STORAGE PORTION

(71) Applicant: Philip Morris USA Inc., Richmond, VA (US)

(72) Inventors: Michel Thorens, Moudon (CH); Jean-Marc Flick, Pomy (CH); Olivier Yves Cochand, Dombresson (CH)

(73) Assignee: PHILIP MORRIS USA INC., Richmond, VA (US)

(*) Notice: Subject to any disclaimer, the term of this patent is extended or adjusted under 35 U.S.C. 154(b) by 352 days.

This patent is subject to a terminal disclaimer.

(21) Appl. No.: 17/193,517

(22) Filed: Mar. 5, 2021

(65) Prior Publication Data

US 2021/0186105 A1 Jun. 24, 2021

Related U.S. Application Data

(60) Continuation of application No. 15/928,387, filed on Mar. 22, 2018, now Pat. No. 10,966,464, which is a
(Continued)

(30) Foreign Application Priority Data

Apr. 30, 2008 (EP) .................................... 08251579

(51) Int. Cl.
*A24D 3/18* (2006.01)
*A24F 40/10* (2020.01)
(Continued)

(52) U.S. Cl.
CPC ................ *A24D 3/18* (2013.01); *A24F 40/42* (2020.01); *A24F 40/44* (2020.01); *A24F 40/46* (2020.01);
(Continued)

(58) Field of Classification Search
CPC .......... A24F 40/10; A24F 40/42; A24F 40/44; A24F 40/46; A61M 15/06
See application file for complete search history.

(56) References Cited

U.S. PATENT DOCUMENTS 1,514,682 A 11/1924 Wilson
1,771,366 A 7/1930 Wyss et al.
(Continued)

FOREIGN PATENT DOCUMENTS

BE 421623 A 6/1937
CA 1202378 A 3/1986
(Continued)

OTHER PUBLICATIONS

"Brazing Ceramic Oxides to Metals at Low Temperatures" by J.P Hammond et al., published in Welding Research Supplement, 227-232-s, (1988).
(Continued)

*Primary Examiner* — Kathryn E Ditmer
(74) *Attorney, Agent, or Firm* — Harness, Dickey & Pierce, P.L.C.

(57) ABSTRACT

An electrically heated smoking system includes a shell and a replaceable mouthpiece. The shell includes an electric power supply and electric circuitry. The mouthpiece includes a liquid storage portion and a capillary wick having a first end and a second end. The first end of the wick extends into the liquid storage portion for contact with liquid therein. The mouthpiece also includes a heating element for heating the second end of the capillary wick, an air outlet, and an aerosol forming chamber between the second end of the capillary wick and the air outlet. When the shell and mouthpiece are engaged or connected, the heating element is in electrical connection with the power supply via the circuitry, and a flowpath for air is defined from at least one air inlet to the air outlet via the aerosol forming chamber. In
(Continued)

use, liquid is transferred from the liquid storage portion towards the heating element by capillary action in the wick. Liquid at the second end of the capillary wick is vaporized by the heating element. The supersaturated vapor created, is mixed and carried in the air flow from the at least one air inlet to the aerosol forming chamber. In the aerosol forming chamber, the vapor condenses to form an aerosol, which is carried towards the air outlet.

16 Claims, 2 Drawing Sheets

Related U.S. Application Data continuation of application No. 15/001,596, filed on Jan. 20, 2016, now abandoned, which is a continuation of application No. 14/324,473, filed on Jul. 7, 2014, now abandoned, which is a division of application No. 12/432,215, filed on Apr. 29, 2009, now Pat. No. 8,794,231.

(51) Int. Cl.
*A24F 40/42* (2020.01)
*A24F 40/44* (2020.01)
*A24F 40/46* (2020.01)
*A24F 40/485* (2020.01)
*A61M 15/06* (2006.01)
*H05B 3/00* (2006.01)

(52) U.S. Cl.
CPC ........... *A24F 40/485* (2020.01); *A61M 15/06* (2013.01); *H05B 3/00* (2013.01); *A24F 40/10* (2020.01)

(56) References Cited

U.S. PATENT DOCUMENTS

| | | |
|---|---|---|
| 1,944,821 A | 1/1934 | Blaise |
| 1,968,509 A | 7/1934 | Tiffany |
| 2,057,353 A * | 10/1936 | Whittemore, Jr. ............ 392/404 |
| 2,104,266 A | 1/1938 | McCormick |
| 2,283,952 A | 5/1942 | Katase |
| 2,406,275 A | 8/1946 | Wejnarth |
| 2,442,004 A | 5/1948 | Hayward-Butt |
| 2,445,237 A | 7/1948 | Stone |
| 2,445,347 A | 7/1948 | Ehlinger |
| 2,609,230 A | 9/1952 | Raleigh |
| 2,898,649 A | 8/1959 | Murray |
| 2,907,686 A | 10/1959 | Siegel |
| 2,971,039 A | 2/1961 | Western |
| 2,974,669 A | 3/1961 | Ellis |
| 3,200,819 A | 8/1965 | Gilbert |
| 3,234,357 A | 2/1966 | Seuthe |
| 3,255,760 A | 6/1966 | Selker |
| 3,258,015 A | 6/1966 | Ellis et al. |
| 3,356,094 A | 12/1967 | Ellis et al. |
| 3,363,633 A | 1/1968 | Weber |
| 3,402,723 A | 9/1968 | Hu |
| 3,482,580 A | 12/1969 | Hollabaugh |
| 3,521,643 A | 7/1970 | Toth |
| 3,559,300 A | 2/1971 | Fox |
| 3,608,560 A | 9/1971 | Briskin et al. |
| 3,681,018 A | 8/1972 | Karl-Georg et al. |
| 3,738,374 A | 6/1973 | Bennett |
| 3,744,496 A | 7/1973 | McCarty et al. |
| 3,804,100 A | 4/1974 | Fariello |
| 3,835,292 A | 9/1974 | Walter et al. |
| 3,875,476 A | 4/1975 | Crandall et al. |
| 3,878,041 A | 4/1975 | Leitnaker et al. |
| 3,889,690 A | 6/1975 | Guarnieri |
| 3,895,219 A | 7/1975 | Richerson et al. |
| 3,943,941 A | 3/1976 | Boyd et al. |
| 4,016,061 A | 4/1977 | Wasa et al. |
| 4,068,672 A | 1/1978 | Guerra |
| 4,077,784 A | 3/1978 | Vayrynen |
| 4,083,372 A | 4/1978 | Boden |
| 4,098,725 A | 7/1978 | Yamamoto et al. |
| 4,110,260 A | 8/1978 | Yamamoto et al. |
| 4,131,119 A | 12/1978 | Blasutti |
| 4,141,369 A | 2/1979 | Burruss |
| 4,164,230 A | 8/1979 | Pearlman |
| 4,193,411 A | 3/1980 | Faris et al. |
| 4,215,708 A | 8/1980 | Bron |
| 4,219,032 A | 8/1980 | Tabatznik et al. |
| 4,246,913 A | 1/1981 | Ogden et al. |
| 4,256,945 A | 3/1981 | Carter et al. |
| 4,259,970 A | 4/1981 | Green, Jr. |
| 4,303,083 A | 12/1981 | Burruss, Jr. |
| 4,319,591 A | 3/1982 | Keith et al. |
| 4,327,186 A | 4/1982 | Murata et al. |
| 4,340,072 A | 7/1982 | Bolt et al. |
| 4,393,884 A | 7/1983 | Jacobs |
| 4,407,971 A | 10/1983 | Komatsu et al. |
| 4,416,840 A | 11/1983 | Lee et al. |
| 4,419,302 A | 12/1983 | Nishino et al. |
| 4,431,903 A | 2/1984 | Riccio |
| 4,436,100 A | 3/1984 | Green, Jr. |
| 4,449,039 A | 5/1984 | Fukazawa et al. |
| 4,463,247 A | 7/1984 | Lawrence et al. |
| 4,475,029 A | 10/1984 | Yoshida et al. |
| 4,503,319 A | 3/1985 | Moritoki et al. |
| 4,505,282 A | 3/1985 | Cogbill et al. |
| 4,515,763 A | 5/1985 | Boudart et al. |
| 4,528,121 A | 7/1985 | Matsushita et al. |
| 4,549,905 A | 10/1985 | Yamaguchi et al. |
| 4,555,358 A | 11/1985 | Matsushita et al. |
| 4,562,337 A | 12/1985 | Lawrence |
| 4,570,646 A | 2/1986 | Herron |
| 4,580,583 A | 4/1986 | Green, Jr. |
| 4,621,649 A | 11/1986 | Osterrath |
| 4,623,401 A | 11/1986 | Derbyshire et al. |
| 4,624,828 A | 11/1986 | Alexander |
| 4,634,837 A | 1/1987 | Ito et al. |
| 4,637,407 A | 1/1987 | Bonanno et al. |
| 4,659,912 A | 4/1987 | Derbyshire |
| 4,708,151 A | 11/1987 | Shelar |
| 4,714,082 A | 12/1987 | Banerjee et al. |
| 4,735,217 A | 4/1988 | Gerth et al. |
| 4,765,347 A | 8/1988 | Sensabaugh, Jr. et al. |
| 4,771,796 A | 9/1988 | Myer |
| 4,776,353 A | 10/1988 | Lilja et al. |
| 4,780,299 A | 10/1988 | Kumagai et al. |
| 4,784,978 A | 11/1988 | Ogasawara et al. |
| 4,793,365 A | 12/1988 | Sensabaugh, Jr. et al. |
| 4,799,979 A | 1/1989 | Baldi |
| 4,800,183 A | 1/1989 | Quinby |
| 4,837,421 A | 6/1989 | Luthy |
| 4,846,199 A | 7/1989 | Rose |
| 4,848,376 A | 7/1989 | Lilja et al. |
| 4,851,206 A | 7/1989 | Boudart et al. |
| 4,874,924 A | 10/1989 | Yamamoto et al. |
| 4,877,989 A | 10/1989 | Drews et al. |
| 4,922,901 A | 5/1990 | Brooks et al. |
| 4,945,929 A | 8/1990 | Egilmex |
| 4,945,931 A | 8/1990 | Gori |
| 4,947,874 A | 8/1990 | Brooks et al. |
| 4,947,875 A | 8/1990 | Brooks et al. |
| 4,966,171 A | 10/1990 | Serrano et al. |
| 4,981,522 A | 1/1991 | Nichols et al. |
| 4,991,606 A | 2/1991 | Serrano et al. |
| 4,993,436 A | 2/1991 | Bloom, Jr. |
| 5,016,656 A | 5/1991 | McMurtrie |
| 5,040,552 A | 8/1991 | Schleich et al. |
| 5,042,510 A | 8/1991 | Curtiss et al. |
| 5,045,237 A | 9/1991 | Washburn |
| 5,060,671 A | 10/1991 | Counts et al. |
| 5,076,296 A | 12/1991 | Nystrom et al. |
| 5,085,804 A | 2/1992 | Washburn |
| 5,093,894 A | 3/1992 | Deevi et al. |
| 5,095,921 A | 3/1992 | Losee et al. |

(56) References Cited

U.S. PATENT DOCUMENTS

| | | | |
|---|---|---|---|
| 5,139,594 A | 8/1992 | Rabin | |
| 5,144,962 A | 9/1992 | Counts et al. | |
| 5,157,242 A | 10/1992 | Hetherington et al. | |
| 5,159,940 A | 11/1992 | Hayward et al. | |
| 5,179,966 A | 1/1993 | Losee et al. | |
| 5,188,130 A | 2/1993 | Hajaligol et al. | |
| 5,224,498 A | 7/1993 | Deevi et al. | |
| 5,228,460 A | 7/1993 | Sprinkel et al. | |
| 5,235,157 A | 8/1993 | Blackburn | |
| 5,249,586 A | 10/1993 | Morgan et al. | |
| 5,269,327 A | 12/1993 | Counts et al. | |
| 5,274,214 A | 12/1993 | Blackburn | |
| 5,285,050 A | 2/1994 | Blackburn | |
| 5,322,075 A | 6/1994 | Deevi et al. | |
| 5,353,813 A | 10/1994 | Deevi et al. | |
| 5,369,723 A | 11/1994 | Counts et al. | |
| 5,388,574 A | 2/1995 | Ingebrethsen | |
| 5,388,594 A | 2/1995 | Counts et al. | |
| 5,396,911 A | 3/1995 | Casey, III et al. | |
| 5,408,574 A | 4/1995 | Deevi et al. | |
| 5,498,855 A | 3/1996 | Deevi et al. | |
| 5,505,214 A | 4/1996 | Collins et al. | |
| 5,514,630 A | 5/1996 | Willkens et al. | |
| 5,591,368 A | 1/1997 | Fleischhauer et al. | |
| 5,613,504 A | 3/1997 | Collins et al. | |
| 5,665,262 A | 9/1997 | Hajaligol et al. | |
| 5,666,947 A | 9/1997 | McKay | |
| 5,865,185 A | 2/1999 | Collins et al. | |
| 5,878,752 A | 3/1999 | Adams et al. | |
| 5,894,841 A | 4/1999 | Voges | |
| 5,935,975 A | 8/1999 | Rose et al. | |
| 6,102,688 A * | 8/2000 | Mifune | F23Q 2/44 431/298 |
| 6,155,268 A | 12/2000 | Takeuchi | |
| 6,196,218 B1 | 3/2001 | Voges | |
| 6,357,534 B1 | 3/2002 | Buetow et al. | |
| 6,598,607 B2 | 7/2003 | Adiga et al. | |
| 6,715,487 B2 | 4/2004 | Nichols et al. | |
| 6,772,756 B2 | 8/2004 | Shayan | |
| 6,810,883 B2 | 11/2004 | Felter et al. | |
| 6,854,470 B1 | 2/2005 | Pu | |
| 7,131,599 B2 | 11/2006 | Katase | |
| 7,147,170 B2 | 12/2006 | Nguyen et al. | |
| 7,167,641 B2 | 1/2007 | Tam et al. | |
| 7,458,374 B2 | 12/2008 | Hale et al. | |
| D590,988 S | 4/2009 | Hon | |
| D590,989 S | 4/2009 | Hon | |
| D590,990 S | 4/2009 | Hon | |
| D590,991 S | 4/2009 | Hon | |
| 7,527,059 B2 | 5/2009 | Iannuzzi | |
| 7,614,402 B2 | 11/2009 | Gomes | |
| 7,726,320 B2 | 6/2010 | Robinson et al. | |
| 7,832,410 B2 | 11/2010 | Hon | |
| 7,845,359 B2 | 12/2010 | Montaser | |
| 7,920,777 B2 | 4/2011 | Rabin et al. | |
| 7,997,280 B2 | 8/2011 | Rosenthal | |
| 8,079,371 B2 | 12/2011 | Robinson et al. | |
| 8,127,772 B2 | 3/2012 | Montaser | |
| 8,156,944 B2 | 4/2012 | Han | |
| 8,365,742 B2 | 2/2013 | Hon | |
| 8,371,310 B2 | 2/2013 | Brenneise | |
| 8,375,957 B2 | 2/2013 | Hon | |
| 8,550,069 B2 | 10/2013 | Alelov | |
| 8,794,231 B2 | 8/2014 | Thorens et al. | |
| 2003/0136407 A1 | 7/2003 | Matsuyama | |
| 2004/0020500 A1 | 2/2004 | Wrenn et al. | |
| 2004/0099266 A1 | 5/2004 | Cross et al. | |
| 2005/0016550 A1 | 1/2005 | Katase | |
| 2005/0268911 A1 | 12/2005 | Cross et al. | |
| 2006/0170119 A1 | 8/2006 | Schwarz | |
| 2006/0191546 A1 | 8/2006 | Takano et al. | |
| 2006/0196518 A1 | 9/2006 | Hon | |
| 2007/0048173 A1 | 3/2007 | Keller et al. | |
| 2007/0102013 A1 | 5/2007 | Adams et al. | |
| 2007/0267031 A1 * | 11/2007 | Hon | A61M 15/06 131/273 |
| 2007/0267032 A1 | 11/2007 | Shan | |
| 2008/0017198 A1 | 1/2008 | Ivri | |
| 2008/0047571 A1 | 2/2008 | Braunshteyn et al. | |
| 2008/0092912 A1 * | 4/2008 | Robinson | A24F 40/42 131/200 |
| 2008/0230052 A1 | 9/2008 | Montaser | |
| 2008/0241255 A1 | 10/2008 | Rose et al. | |
| 2008/0257367 A1 | 10/2008 | Paterno et al. | |
| 2008/0276947 A1 | 11/2008 | Martzel | |
| 2009/0095311 A1 * | 4/2009 | Han | H05B 3/06 131/194 |
| 2009/0126745 A1 | 5/2009 | Hon | |
| 2009/0151717 A1 | 6/2009 | Bowen et al. | |
| 2009/0162294 A1 | 6/2009 | Werner | |
| 2009/0188490 A1 | 7/2009 | Han | |
| 2009/0196587 A1 | 8/2009 | Cheung | |
| 2009/0230117 A1 | 9/2009 | Fernando et al. | |
| 2009/0272379 A1 | 11/2009 | Thorens et al. | |
| 2010/0307518 A1 | 12/2010 | Wang | |
| 2011/0036346 A1 | 2/2011 | Cohen et al. | |
| 2011/0094523 A1 | 4/2011 | Thorens et al. | |
| 2011/0120482 A1 | 5/2011 | Brenneise | |
| 2011/0209717 A1 | 9/2011 | Han | |
| 2011/0232654 A1 | 9/2011 | Mass | |
| 2012/0090630 A1 | 4/2012 | Hon | |

FOREIGN PATENT DOCUMENTS

| | | |
|---|---|---|
| CA | 2749077 A1 | 2/2013 |
| CA | 2720293 C | 11/2016 |
| CN | 87103178 A | 11/1987 |
| CN | 87/104459 A | 2/1988 |
| CN | 1040914 | 4/1990 |
| CN | 1040914 A | 4/1990 |
| CN | 1106812 A | 8/1995 |
| CN | 1205849 A | 1/1999 |
| CN | 1333657 A | 1/2002 |
| CN | 1575135 A | 2/2005 |
| CN | 277799 | 5/2006 |
| CN | 2887086 Y | 4/2007 |
| CN | 200983833 Y | 12/2007 |
| CN | 101116542 A | 2/2008 |
| CN | 201067079 Y | 6/2008 |
| CN | 201085044 Y | 7/2008 |
| CN | 10132257 | 12/2008 |
| CN | 200920001296 | 1/2010 |
| CN | 102014677 B | 2/2017 |
| DE | 3640917 A1 | 8/1988 |
| DE | 3735704 A1 | 5/1989 |
| DE | 19854009 A1 | 5/2000 |
| DE | 69824982 T2 | 10/2004 |
| EA | 009116 | 12/2006 |
| EP | 0893071 A1 | 7/1908 |
| EP | 0117355 A2 | 9/1984 |
| EP | 0236992 A2 | 9/1987 |
| EP | 0277519 A2 | 8/1988 |
| EP | 0295122 A2 | 12/1988 |
| EP | 4 430 559 | 12/1989 |
| EP | 0358002 A2 | 3/1990 |
| EP | 0358114 A2 | 3/1990 |
| EP | 0430559 A2 | 6/1991 |
| EP | 0430566 A2 | 6/1991 |
| EP | 438862 A2 | 7/1991 |
| EP | 0488488 A1 | 6/1992 |
| EP | 0503767 A1 | 9/1992 |
| EP | 0845220 A1 | 6/1998 |
| EP | 0857431 A1 | 8/1998 |
| EP | 1298808 A2 | 4/2003 |
| EP | 1618803 A1 | 1/2006 |
| EP | 1736065 A1 | 12/2006 |
| EP | 1989946 A1 | 11/2008 |
| EP | 2022349 A1 | 2/2009 |
| EP | 2022350 A1 | 2/2009 |
| EP | 2110033 A1 | 10/2009 |
| EP | 2113178 A1 | 11/2009 |
| EP | 2113179 A1 | 11/2009 |
| EP | 2404515 A1 | 1/2012 |

(56) References Cited

FOREIGN PATENT DOCUMENTS

| | | |
|---|---|---|
| EP | 2282649 B1 | 1/2014 |
| GB | 1298808 A | 12/1972 |
| GB | 2132539 A | 7/1984 |
| GB | 2148079 A | 5/1985 |
| GB | 2148676 A | 5/1985 |
| JP | 61-68061 | 4/1986 |
| JP | S62-262981 A | 11/1987 |
| JP | 64-17386 | 1/1989 |
| JP | 03232481 | 10/1991 |
| JP | 33258657 | 12/1991 |
| JP | H11-089551 A | 4/1999 |
| JP | 3277265 B2 | 4/2002 |
| JP | 3325028 B2 | 9/2002 |
| JP | 3392138 B2 | 3/2003 |
| JP | 2005-537918 A | 12/2005 |
| JP | 2006/320286 A | 11/2006 |
| JP | 8-5119666 | 8/2009 |
| JP | 2009-194812 A | 8/2009 |
| JP | 2009-537119 A | 10/2009 |
| JP | 2009-537120 A | 10/2009 |
| KR | 100636287 B1 | 10/2006 |
| RU | 2297781 C2 | 4/2007 |
| WO | WO-86/02528 A1 | 5/1986 |
| WO | WO-9003224 A1 | 4/1990 |
| WO | WO-95/02970 A1 | 2/1995 |
| WO | WO-1998/028994 A1 | 7/1998 |
| WO | WO-00/28843 A1 | 5/2000 |
| WO | WO-2000/050111 A1 | 8/2000 |
| WO | WO-03037412 A2 | 5/2003 |
| WO | WO-03/095688 A2 | 11/2003 |
| WO | WO-2004/043175 A1 | 5/2004 |
| WO | WO-2004/080216 A1 | 9/2004 |
| WO | WO-2004/095955 A1 | 11/2004 |
| WO | WO-2005/099494 A1 | 10/2005 |
| WO | WO-2005120614 A1 | 12/2005 |
| WO | WO-2007024130 A1 | 3/2007 |
| WO | WO-2007/066374 A1 | 6/2007 |
| WO | WO-2007/078273 A1 | 7/2007 |
| WO | WO-2007/098337 A2 | 8/2007 |
| WO | WO-2007/131449 A1 | 11/2007 |
| WO | WO-2007/131450 A1 | 11/2007 |
| WO | WO-2007131449 A1 * 11/2007 ........... A24B 15/167 | |
| WO | WO-2007/141668 A2 | 12/2007 |
| WO | WO-2008/055423 A1 | 5/2008 |
| WO | WO-2010091593 A1 | 8/2010 |

OTHER PUBLICATIONS

"Brazing of Titanium-Vapor-Coated Silicon Nitride" by M. L. Santella, published in Advanced Ceramic Materials, 3(5):457-465 (1988).
"Characterizing Thermal Spray Coatings", Article based on presentation made at the Fourth National Thermal Spray Conference, May 4-10, 1991 and appearing in Advanced Materials and Processes, May 1992, pp. 23-27.
"Excerpt from 'NASA Tech Briefs'," Jul./Aug. 1988, p. 31.
"High Temperature Structural Silicides" by A.K. Vasudevan et al., Elsevier Science Publishers B.V. (1992).
"Joining of Ceramics" by R.E. Loehman et al., published in Ceramic Bulletin, 67(d); 375-380 (1988).
"Microstructure of Alumina Brazed with a Silver-Cooper-Titanium Alloy" by M.L. Santella et al., published in J. Am. Ceram. Soc., 73(6):1785-1787 (1990).
European Search Report dated Mar. 11, 2010 for European Application No. 09252490.
European Search Report of Application No. 08251579.2-2313 dated Nov. 7, 2008.
Fen et al., "Cyclic oxidation of Haynes 230 alloy", Chapman & Hall, pp. 1514-1520 (1992).
Howes, Jr., "Computerized Plasma Control for Applying Medical-Quality Coatings", Industrial Heaing, pp. 22-25, Aug. 1993.

International Preliminary Report on Patentability dated May 10, 2012 for PCT/EP2010/006534.
International Search Report and Written Opinion dated Apr. 5, 2011 for PCT/EP2010/006534.
John A. Dean, Lange's handbook of Chemistry, 12th Edition, 1978 pp. 4-16, 4-123.
K.H. Jack, "Binary and ternary interstitial alloys 1. The iron-nitrogen system: the structures of Fe4N and Fe2N", Proceedings of the Royal Society, A. 195, pp. 34-40 (1948).
K.H. Jack, "The Iron-Nitrogen System: The Crystal Structures of G-Phase Iron Nitrides", Aceta Crystallographica, 5. pp. 404-411 (1952).
K.H. Jack, "The iron-nitrogen system: the preparation and the crystal structures of nitrogen-austenite (V) and nitrogen-martensite (a)", Proceedings of the Royal Society, A. 208, pp. 200-215 (1952).
Kutner, "Thermal spray by design", Reprint from Advanced Materials & Processes Incorporating Metal Progress, Oct. 1988.
Oxidation Behavior of Silver- and Copper-Based Brazing Filler Metals for Silicon Nitride/Metal Joints by R.R. Kapoor et al., published in J. Am. Ceram. Soc., 72(3):448-454 (1989).
Reinshagen and Sikka, "Thermal Spraying of Selected Aluminides", Proceedings of the Fourth National Thermal Spray Conference, Pittsburgh, PA USA, pp. 307-313 (May 4-10, 1991).
V. Sikka, "Processing of Aluminides", Intermetallic Metallurgy and Processing Intermetallic Compounds, ed Stoloff et al., Van Mestrand Reinhold, N.Y., 1994.
Notice of Opposition dated Oct. 16, 2014 filed in corresponding European Patent No. EP2282649 (Application No. EP09737837.6).
U.S. Office Action dated Jun. 14, 2018 for corresponding U.S. Appl. No. 15/001,596.
Corrected First Action Interview Pilot Program Pre-Interview Communication dated Jun. 12, 2018 for U.S. Appl. No. 15/928,387 (replaces Office Action dated Jun. 11, 2018).
Australian Office Action dated Dec. 5, 2013.
Canadian Office Action dated Jul. 14, 2015.
Chinese Office Action and English translation thereof dated Jan. 31, 2012.
Chinese Office Action and Search Report and English translation thereof dated Oct. 19, 2012.
Chinese Office Action and Search Report and English translation thereof dated Jun. 13, 2013.
Chinese Rejection Decision and English translation thereof dated Nov. 26, 2013.
Chinese Notification of Reexamination and English translation thereof dated Jun. 25, 2015.
Chinese Decision of Patent Reexamination Board dated Jan. 27, 2016.
Chinese Office Action and Search Report and English translation thereof dated Apr. 29, 2016.
Colombian Office Action and English translation thereof dated Apr. 16, 2013.
European Search Report dated Nov. 7, 2008.
European Office Action dated Nov. 26, 2012.
European Notice of Opposition dated Oct. 8, 2014.
European Summons to Attend Oral Proceedings and Preliminary Non-Binding Opinion dated Jan. 29, 2016.
European Written Submissions prior to Oral Proceedings dated Oct. 28, 2016.
European Interlocutory Decision dated Jan. 11, 2017.
European Reply to Appeal dated Dec. 8, 2017.
European Search Report dated Mar. 5, 2014.
European Third Part Observations dated Aug. 19, 2016.
European Office Action dated Dec. 19, 2016.
European Office Action dated Aug. 2, 2018.
Gulf Co-operation Council Office Action dated Sep. 22, 2013.
Gulf Co-operation Council Office Action and Search report dated Sep. 7, 2016.
Gulf Co-operation Council Office Action dated Dec. 29, 2016.
Israel Office Action dated Feb. 26, 2013.
Indian Office Action dated Feb. 12, 2018.
Japanese Office Action and English translation thereof dated Jul. 10, 2013.

(56) References Cited

OTHER PUBLICATIONS

Japanese Decision to Grant and English translation thereof dated Feb. 3, 2014.
Japanese Office Action and English translation thereof dated Mar. 2, 2015.
Japanese Decision to Grant and English translation thereof dated Jan. 18, 2016.
Japanese Opposition dated Oct. 18, 2016.
Japanese First Notification of Reasons for Revocation dated Nov. 18, 2016.
Japanese Further Arguments by the Opponent dated Apr. 25, 2017.
Japanese Second Notification of Reasons for Revocation dated Apr. 26, 2017.
Korean Notice of Allowance and English translation thereof Jan. 15, 2016.
Korean Office Action and English translation thereof Feb. 13, 2016.
Korean Notice of Allowance and English translation thereof Sep. 23, 2016.
Kazakhstan Office Action and English translation thereof dated Apr. 5, 2013.
Kazakhstan Decision to Grant and English translation thereof dated Aug. 16, 2013.
Mexican Office Action and English translation thereof dated May 22, 2013.
Malaysian Office Action dated Jan. 30, 2015.
New Zealand Office Action dated Feb. 22, 2012.
International Search Report and Written Opinion dated Sep. 4, 2009.
Philippines Office Action dated Sep. 16, 2011.
Philippines Office Action dated Apr. 8, 2013.
Philippines Office Action dated Jun. 5, 2014.
Philippines Office Action dated Feb. 2, 2015.
Russian Office Action and English translation thereof dated Apr. 12, 2013.
Russian Decision to Grant and English translation thereof dated Dec. 19, 2013.
Russian Search Report and English translation thereof dated Dec. 1, 2017.
Russian Decision to Grant and English translation thereof dated Dec. 20, 2017.
Singapore Office Action dated Oct. 10, 2011.
Singapore Office Action dated Aug. 8, 2012.
Taiwan Office Action and Search Report and English translation thereof dated Apr. 16, 2014.
Ukraine Office Action dated Jun. 18, 2012.
Ukraine Notice of Allowance dated Sep. 3, 2012.
Izuru Shinmura, "Kojien," Sixth Edition, Published by Iwanami Shoten, Jan. 11, 2008, p. 2626.
Takashi Kenjo and Hisashi Takahashi, "Denshi Kairo Nyumon Kouza (Electronic Circuit Introduction Course)," Published by Denpa Shinbunnsya, Oct. 10, 2003, pp. 138-139.
Chinese Office Action and English translation thereof dated Nov. 2, 2018.
U.S. Office Action for corresponding U.S. Appl. No. 15/001,596 dated Dec. 26, 2018.
Brazilian Office Action dated Jan. 29, 2019.
Malaysian Office Action dated Apr. 15, 2019.
Brazilian Office Action and English translation thereof dated Jul. 16, 2019.
Brazilian Notice of Allowance dated Nov. 12, 2019.
Gulf Co-operation Council Office Action dated Nov. 25, 2019.
Malaysian Office Action dated May 15, 2020.
Dictionary definition of linear (Year: 2020).
Dictionary definition of filament (Year: 2020).

\* cited by examiner

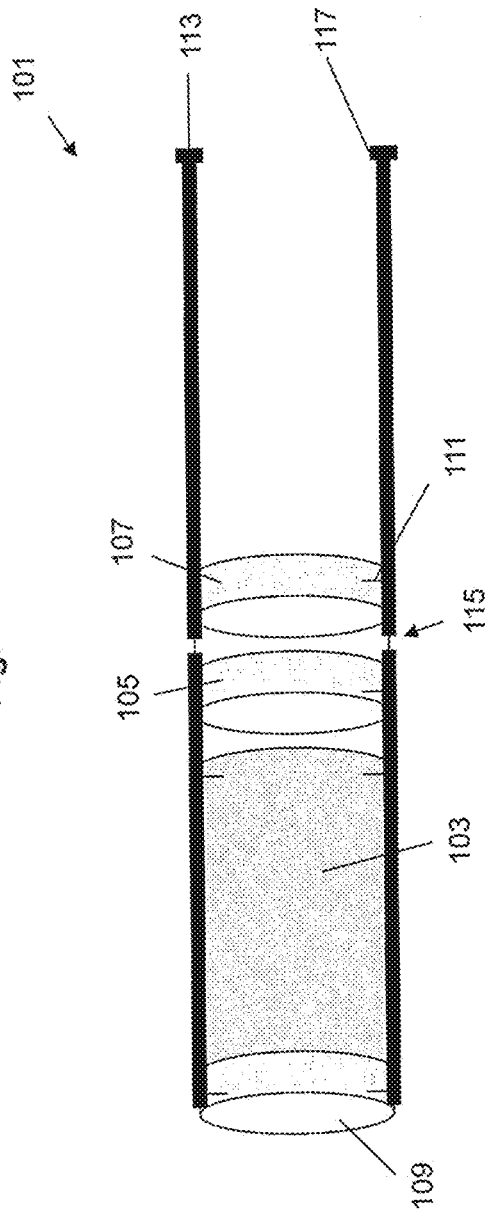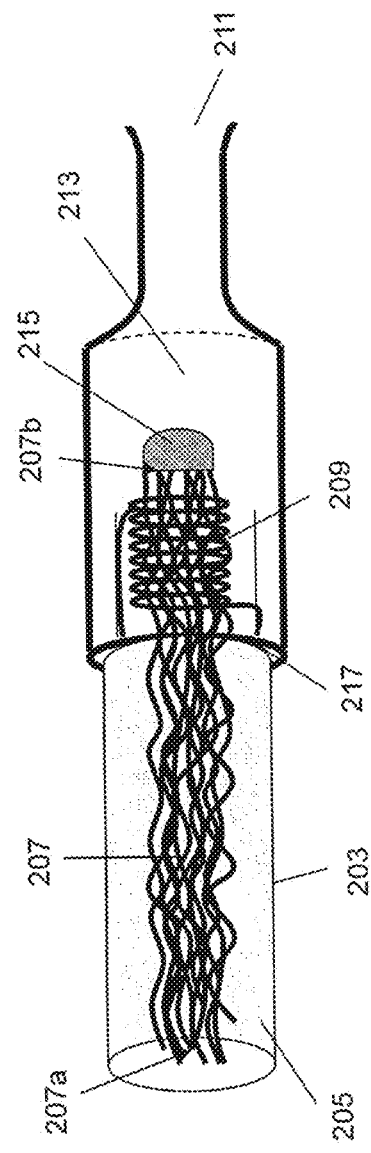

ELECTRICALLY HEATED SMOKING SYSTEM HAVING A LIQUID STORAGE PORTION

CROSS-REFERENCE TO RELATED APPLICATION

This application is a continuation of and claims priority under 35 U.S.C. § 120/121 to application Ser. No. 15/928,387, filed Mar. 22, 2018, which is a continuation application of and claims priority under 35 U.S.C. § 120/121 to application Ser. No. 15/001,596, filed Jan. 20, 2016, which is a continuation application of and claims priority under 35 U.S.C. § 120/121 to application Ser. No. 14/324,473, filed Jul. 7, 2014, which is a divisional application of application Ser. No. 12/432,215, now U.S. Pat. No. 8,794,231, filed Apr. 29, 2009, entitled AN ELECTRICALLY HEATED SMOKING SYSTEM HAVING A LIQUID STORAGE PORTION which corresponds to European Application No. 08 251 579, filed Apr. 30, 2008, the entire contents of each of which is incorporated herein by reference hereto.

BACKGROUND OF THE INVENTION

The present invention relates to an electrically heated smoking system for receiving an aerosol-forming substrate. In particular, the present invention relates to an electrically heated smoking system for receiving an aerosol-forming substrate, in which the aerosol-forming substrate is a liquid.

A number of prior art documents, for example U.S. Pat. No. 5,060,671 (commonly assigned, the entire contents of which are incorporated herein by this reference thereto), U.S. Pat. No. 5,388,594 (commonly assigned, the entire contents of which are incorporated herein by this reference thereto), U.S. Pat. No. 5,505,214 (commonly assigned, the entire contents of which are incorporated herein by this reference thereto), U.S. Pat. No. 5,591,368 (commonly assigned, the entire contents of which are incorporated herein by this reference thereto), WO 2004/043175 (commonly assigned, the entire contents of which are incorporated herein by this reference thereto), EP-A-0 358 002 and WO 2007/131449, disclose electrically operated smoking systems, having a number of advantages. One advantage is that they significantly reduce sidestream smoke, while permitting the smoker to selectively suspend and reinitiate smoking.

Other prior art documents, such as EP-A-0 295 122, EP-A-1 618 803 and EP-A-1 736 065, disclose electrical smoking systems which use a liquid as the aerosol-forming substrate. The liquid may be contained in a cartridge which is receivable in a housing. A power supply, such as a battery, is provided, connected to a heater to heat the liquid substrate during a puff, to form the aerosol which is provided to the smoker.

The electrically heated smoking systems of the prior art, including those described above, do have a number of advantages, but there is still room for improvement. It is therefore an object of the invention to provide an improved electrically heated smoking system.

SUMMARY OF SELECTED ASPECTS OF THE INVENTION

According to a first aspect of the invention, there is provided an electrically heated smoking system comprising a shell and a replaceable mouthpiece, the shell comprising an electric power supply and electric circuitry; the mouthpiece comprising a liquid storage portion, a capillary wick having a first end and a second end, the first end extending into the liquid storage portion for contact with liquid therein, at least one heating element for heating the second end of the capillary wick, an air outlet, and an aerosol forming chamber between the second end of the capillary wick and the air outlet; wherein, when the shell and mouthpiece are engaged, the at least one heating element is in electrical connection with the power supply via the circuitry, and a flow route for air is defined from at least one air inlet to the air outlet via the aerosol forming chamber.

The at least one air inlet may be provided in the shell or in the mouthpiece. In use, liquid is transferred from the liquid storage portion towards the heating element by capillary action in the capillary wick. When the heating element is activated, the liquid at the second end of the capillary wick is vaporized by the heating element to form a supersaturated vapor. The supersaturated vapor is mixed and carried in the air flow from the at least one air inlet to the aerosol forming chamber. In the aerosol forming chamber, the vapor condenses to form an aerosol, which is carried towards the air outlet into the mouth of a user.

The electrically heated smoking system according to the invention provides a number of advantages. Firstly, because the replaceable mouthpiece contains the at least one heating element, the liquid storage portion and the wick, all elements which are potentially in contact with the liquid are changed when the mouthpiece is replaced. There will be no cross-contamination in the shell between different mouthpieces, for example ones using different liquids. In addition, the liquid in the liquid storage portion is protected from oxygen (because oxygen cannot generally enter the liquid storage portion via the capillary wick) and, in some embodiments light, so that the risk of degradation of the liquid is significantly reduced. Therefore, a high level of hygiene can be maintained. Secondly, the mouthpiece structure means that there is a low risk of leakage from the liquid storage portion, which is not the case for many of the electrically heated smoking systems of the prior art. This prevents waste of the liquid, but also makes it difficult for an unauthorized user to access the liquid by dismantling the mouthpiece. Also, if the mouthpiece is replaced at suitable intervals, there is little chance of the heating element becoming clogged with liquid. Finally, using a capillary wick extending between the liquid and the heating element allows the structure of the mouthpiece to be relatively simple. There is preferably only one capillary mechanism in the system.

The at least one heating element may comprise a single heating element. Alternatively, the at least one heating element may comprise more than one heating element, for example two, three, four, five, six or more heating elements. The heating element or heating elements may be arranged appropriately so as to most effectively vaporize liquid at the second end of the capillary wick.

The at least one heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminum-titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal and iron-manganese-aluminum based alloys. In composite materials, the electrically resistive material may optionally be embedded in, encapsulated or coated with an insulating material or vice-versa, depending on the kinetics of energy transfer and the external physicochemical properties required. Examples of suitable composite heating elements are disclosed in U.S. Pat. No. 5,498,855 (commonly assigned, the entire contents of which are incorporated herein by this reference thereto), WO 03/095688 and U.S. Pat. No. 5,514,630.

The at least one heating element may take any suitable form. For example, the at least one heating element may take the form of a heating blade, such as those described in U.S. Pat. Nos. 5,388,594, 5,591,368 and 5,505,214. Alternatively, the at least one heating element may take the form of a casing or substrate having different electro-conductive portions, as described in EP-A-1 128 741, or an electrically resistive metallic tube, as described in WO 2007/066374. Alternatively, the at least one heating element may be a disk (end) heater or a combination of a disk heater with heating needles or rods. Alternatively, the at least one heating element may take the form of a metallic etched foil insulated between two layers of an inert material. In that case, the inert material may comprise Kapton, all-polyimide or mica foil. Alternatively, the at least one heating element may take the form of a sheet of material, which may be rolled around the second end of the capillary wick. The sheet may be made from any suitable material, for example an iron-aluminum based alloy, an iron-manganese-aluminum base alloy or Timetal. The sheet may be rectangular in shape, or may have a patterned shape which may form a coil-like structure when rolled around the second end of the capillary wick. Other alternatives include a heating wire or filament, for example a Ni—Cr, platinum, tungsten or alloy wire, such as those described in EP-A-1 736 065, or a heating plate.

In a preferred embodiment, the at least one heating element comprises a coil of wire surrounding the second end of the capillary wick. In that embodiment, the wire is preferably a metal wire. Even more preferably, the wire is a metal alloy wire. The heating element may completely or partially encircle the second end of the capillary wick.

The at least one heating element may heat the liquid at the second end of the capillary wick by means of conduction. The heating element may be at least partially in contact with the second end of the wick. Alternatively, heat from the heating element may be conducted to the liquid by means of a heat conductive element. Alternatively, the at least one heating element may transfer heat to the incoming ambient air that is drawn through the electrically heated smoking system during use, which in turn heats the liquid by convection. The ambient air may be heated before passing through the system. Alternatively, the ambient air may be first drawn through the second end of the wick and then heated, as described in WO 2007/078273.

Preferably, the electric circuitry comprises a sensor to detect air flow indicative of a user taking a puff. The sensor may be an electro-mechanical device. Alternatively, the sensor may be any of: a mechanical device, an optical device, an opto-mechanical device and a micro electro mechanical systems (MEMS) based sensor. In that case, preferably, the electric circuitry is arranged to provide an electric current pulse to the at least one heating element when the sensor senses a user taking a puff. Preferably, the time-period of the electric current pulse is pre-set, depending on the amount of liquid desired to be vaporized. The electric circuitry is preferably programmable for this purpose.

Alternatively, the electric circuitry may comprise a manually operable switch for a user to initiate a puff. In that case, preferably, the electric circuitry is arranged to provide an electric current pulse to the at least one heating element when the user initiates a puff. The time-period of the electric current pulse is preferably pre-set depending on the amount of liquid desired to be vaporized. The electric circuitry is preferably programmable for this purpose.

Preferably, the at least one air inlet is in the shell. Alternatively, the at least one air inlet may be in the mouthpiece. In one embodiment, the at least one air inlet comprises two air inlets. Alternatively, there may be three, four, five or more air inlets. Preferably, if there is more than one air inlet, the air inlets are spaced around the shell or around the mouthpiece. In a preferred embodiment, the electric circuitry comprises a sensor to detect air flow indicative of a user taking a puff, and the at least one inlet is in the shell, upstream of the sensor.

Preferably, the electric power supply comprises a cell contained in the shell. The electric power supply may be a lithium-ion battery or one of its variants, for example a lithium-ion polymer battery. Alternatively, the power supply may be a nickel-metal hydride battery or a nickel cadmium battery or a fuel cell. In that case, preferably, the electrically heated smoking system is usable by a smoker until the energy in the power cell is used up.

Alternatively, the electric power supply may comprise circuitry chargeable by an external charging portion. In that case, preferably the circuitry, when charged, provides power for a pre-determined number of puffs, after which the circuitry must be re-connected to the external charging portion. An example of suitable circuitry is one or more capacitors or rechargeable batteries.

Preferably, the shell further comprises a puff indicator for indicating when the heating element is activated. In the embodiment in which the electric circuitry comprises a sensor to detect air flow indicative of a user taking a puff, the indicator may be activated when the sensor senses air flow indicative of the user taking a puff. In the embodiment in which the electric circuitry comprises a manually operable switch, the indicator may be activated by the switch.

Preferably, the shell and mouthpiece are arranged to releasably lock together when engaged.

Preferably, the liquid storage portion is not refillable. Thus, when the liquid in the liquid storage portion has been used up, the entire mouthpiece is replaced. Alternatively, the liquid storage portion may be refillable. In that case, the mouthpiece may be replaced after a certain number of refills of the liquid storage portion. Preferably, the liquid storage portion is arranged to hold liquid for a pre-determined number of puffs.

The liquid has physical properties, including viscosity, which allow the liquid to be transported through the capillary wick by capillary action. The liquid has a boiling point suitable for use in the electrically heated smoking system: if the boiling point is too high, the heating element will not be able to vaporize liquid at the second end of the capillary wick, but, if the boiling point is too low, the liquid may vaporize even without the heating element being activated. The liquid preferably comprises a tobacco-containing material comprising volatile tobacco flavour compounds which are released from the liquid upon heating. Alternatively, or in addition, the liquid may comprise a non-tobacco material. The liquid may include water, solvents, ethanol, plant extracts and natural or artificial flavours. Preferably, the liquid further comprises an aerosol former. Examples of suitable aerosol formers are glycerine and propylene glycol. Additional examples of potentially suitable aerosol formers are described in EP-A-0 277 519 and U.S. Pat. No. 5,396,911.

The liquid storage portion is preferably a container. For example, the container may be a container such as that described in EP-A-0 893 071. Preferably, the liquid storage portion does not include any porous materials, so that there is only a single capillary mechanism (the capillary wick) in the electrically heated smoking system. This keeps the structure of the mouthpiece simple and the entire system low-maintenance. Preferably, the container is opaque, thereby limiting degradation of the liquid by light.

The electrically heated smoking system may further comprise an atomizer including the at least one heating element. In addition to the heating element, the atomizer may include one or more electromechanical elements such as piezoelectric elements. Additionally or alternatively, the atomizer may also include elements that use electrostatic, electromagnetic or pneumatic effects.

The capillary wick may have a fibrous or spongy structure. For example, the capillary wick may comprise a plurality of fibers or threads, generally aligned in the longitudinal direction of the smoking system, or sponge-like material formed into a rod shape along the longitudinal direction of the smoking system. The structure of the wick forms a plurality of small bores or tubes, through which the liquid can be transported from the liquid storage portion to the heating element, by capillary action. The capillary wick may comprise any suitable material or combination of materials. Examples of suitable materials are ceramic- or graphite-based materials in the form of fibers or sintered powders. The capillary wick may have any suitable capillarity and porosity so as to be used with different liquid physical properties such as density, viscosity, surface tension and vapor pressure.

The shell may comprise any suitable material or combination of materials. Examples of suitable materials include metals, alloys, plastics or composite materials containing one or more of those materials. Preferably, the material is light and non-brittle.

The mouthpiece may comprise any suitable material or combination of materials. Examples of suitable materials include thermoplastics that are suitable for food or pharmaceutical applications, for example polypropylene, polyetheretherketone (PEEK) and polyethylene.

Preferably, the electrically heated smoking system is portable. The electrically heated smoking system may have a size comparable to a conventional cigar or cigarette.

According to a second aspect of the invention, there is provided a mouthpiece for engaging with a shell to form an electrically heated smoking system, the shell having an electric power supply and electric circuitry, the mouthpiece comprising: a liquid storage portion; a capillary wick having a first end and a second end, the first end extending into the liquid storage portion for contact with liquid therein; at least one heating element for heating the second end of the capillary wick; an air outlet; and an aerosol forming chamber between the second end of the capillary wick and the air outlet, wherein, when the shell and mouthpiece are engaged, the at least one heating element is in electrical connection with the power supply via the circuitry, and a flowpath or flow route for air is defined from at least one air inlet to the air outlet via the aerosol forming chamber.

In a preferred embodiment, the at least one heating element comprises a coil of wire surrounding the second end of the capillary wick. In that embodiment, preferably the wire is a metal alloy wire.

According to the invention, there is also provided a shell arranged to engage with the mouthpiece of the second aspect of the invention.

According to a third aspect of the invention, there is provided a shell for engaging with a mouthpiece to form an electrically heated smoking system, the mouthpiece having a liquid storage portion, a capillary wick having a first end and a second end, the first end extending into the liquid storage portion for contact with liquid therein, at least one heating element for heating the second end of the capillary wick, an air outlet, and an aerosol forming chamber between the second end of the capillary wick and the air outlet, the shell comprising: an electric power supply; and electric circuitry, wherein, when the shell and mouthpiece are engaged, the at least one heating element is in electrical connection with the power supply via the circuitry, and a flow route or flowpath for air is defined from at least one air inlet to the air outlet via the aerosol forming chamber.

Preferably, the electric circuitry comprises a sensor to detect air flow indicative of a user taking a puff.

Preferably, the shell further comprises the at least one air inlet.

According to the invention, there is also provided a mouthpiece arranged to engage with the shell of the third aspect of the invention.

Features described in relation to one aspect of the invention may also be applicable to another aspect of the invention.

BRIEF DESCRIPTION OF THE DRAWINGS

Many objects and advantages of the invention will be further described, by way of example only, with reference to the accompanying drawings, and others will be apparent to those skilled in the art when the accompanying drawings are read in conjunction with this written description. In the accompanying drawings, like reference numerals are applied to like elements and:

FIG. 1 shows a shell of an electrically heated smoking system according to an embodiment of the invention;

FIG. 2 shows a mouthpiece of an electrically heated smoking system according to an embodiment of the invention.

DETAILED DESCRIPTION OF THE PREFERRED EMBODIMENTS

Figure 3:
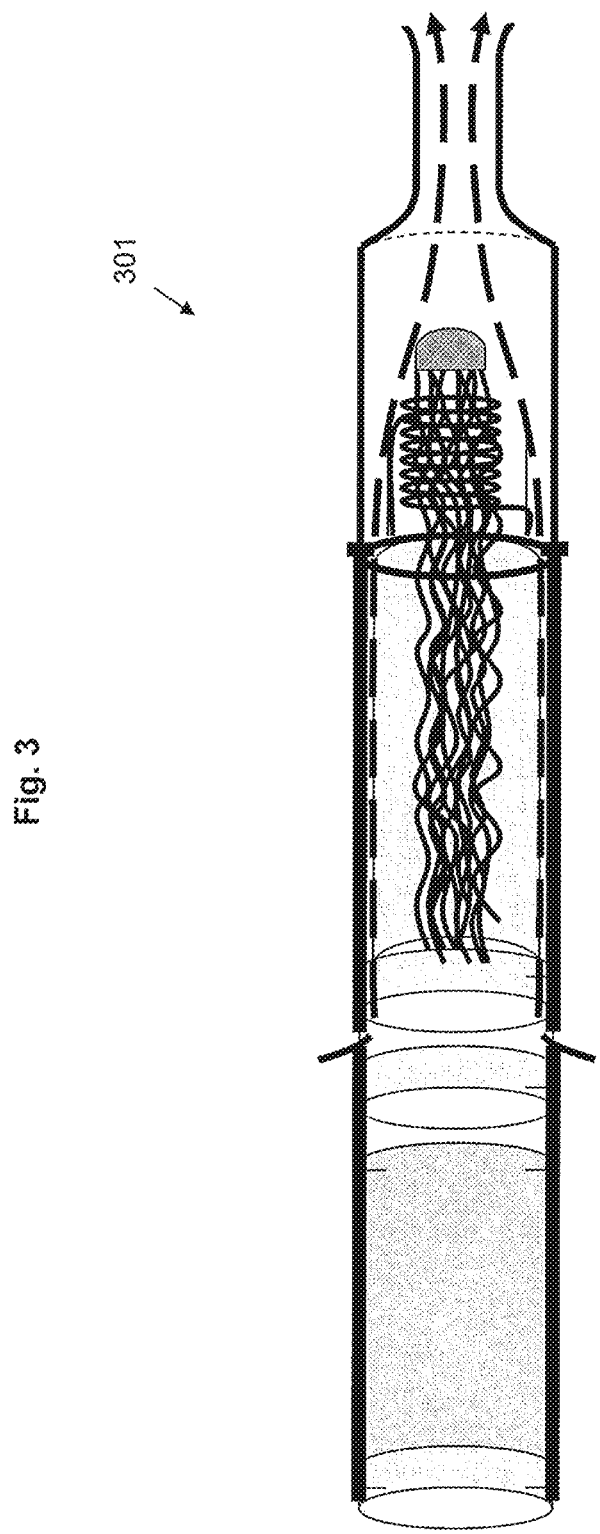
FIG. 3 shows a constructed electrically heated smoking system, comprising the shell of FIG. 1 and the mouthpiece of FIG. 2.

FIG. 1 shows a shell of an electrically heated smoking system according to one embodiment of the invention. The shell 101 comprises an electric power supply in the form of battery 103, electric circuitry in the form of circuitry 105 and puff detection system 107, a puff indicator 109, electrical connections 111, electrical contacts 113, air inlets 115 and a lock mechanism 117. The shell 101 is designed to engage with the mouthpiece 201 of FIG. 2.

FIG. 2 shows a mouthpiece of an electrically heated smoking system according to one embodiment of the invention. The mouthpiece 201 comprises a liquid storage portion in the form of cartridge 203 containing liquid 205, a capillary wick 207, a heating element in the form of heating coil 209, an air outlet 211 and an aerosol forming chamber 213. The first end 207a of the capillary wick 207 extends into the cartridge 203 and the second end 207b of the capillary wick 207 is surrounded by the heating coil 209. The mouthpiece also includes a cap 215 to protect the second end 207b of the capillary wick 207 and an insulation ring 217. The mouthpiece 201 is designed to engage with the shell 101 of FIG. 1.

FIG. 3 shows the shell 101 of FIG. 1 engaged with the mouthpiece 201 of FIG. 2 to form an electrically heated smoking system 301 arranged to supply aerosol to a user on demand. The shell 101 and mouthpiece 201 are releasably locked together by lock mechanism 117. Ends of the heating coil 209 are in contact with the electrical contacts 113 on the shell. Operation of the system 301 is as follows.

Liquid 205 is transferred from the cartridge 203 from the first end 207a of the wick 207 to the second end 207b of the wick by capillary action. When the user draws on the device at the air outlet 211, ambient air is drawn through air inlets 115. In this embodiment, the puff detection system 107 senses the puff and activates the heating coil 209 and switches on the puff indicator 109. The battery 103 supplies a pulse of energy to the heating coil 209 to heat the second end 207b of the wick 207. The liquid in the second end 207b of the wick 207 is vaporized by the heating coil 209 to create a supersaturated vapor. At the same time, the liquid being vaporized is replaced by further liquid moving towards the second end 207b of wick by capillary action. (This is sometimes referred to as "pumping action".) The supersaturated vapor created is mixed with and carried in the air flow from the air inlets 115 towards the aerosol forming chamber 213. In the aerosol forming chamber 213, the vapor condenses to form an inhalable aerosol, which is carried towards the outlet 211 and into the mouth of a user.

In this embodiment, the circuitry 105 and the puff detection system 107 are programmable. The circuitry 105 and puff detection system 107 can be used to manage the device operation. In this embodiment, when the puff detection system 107 senses the user taking a puff, the battery supplies a current pulse of a pre-determined time to the heating coil 209. The pre-determined time for the current pulse will depend on the amount of liquid required for a single puff, and the time taken for that amount of liquid to be vaporized. That will, in turn, depend on the properties of the liquid, the heating coil and the capillary wick. The pre-determined time may be between about 0.5 and about 3 seconds.

In this embodiment, the cartridge 203 in the mouthpiece is sized so as to contain sufficient liquid for a pre-determined number of puffs. After that pre-determined number of puffs, the cartridge could be refilled, but preferably the entire mouthpiece is replaced. The pre-determined number of puffs is ideally between about 200 and about 2000 puffs and this will depend on the desired size of the cartridge, mouthpiece and entire device, and the properties of the liquid being used. The cartridge 203 can be made from any suitable material. Examples include glass and plastic polymers such as PET or others used in the pharmaceutical or food industries. The material should be chosen so as to avoid leakage, breakage or abuse, as far as possible.

In the embodiment shown in FIGS. 1 to 3, when the shell and mouthpiece are engaged, the cartridge 203 is positioned upstream of the second end 207b of the wick and the heating coil 209. Thus, ambient air is drawn through air inlets 115 and passes around the cartridge 203 before reaching the second end 207b of the wick and the heating coil 209. However, in an alternative embodiment, the mouthpiece may be structured such that, when the shell and mouthpiece are engaged, the cartridge is positioned downstream of the second end of the wick and the heating coil. In that embodiment, the ambient air will be drawn through the air inlets, then the vapor or aerosol will pass around the cartridge on the way to the air outlet.

The capillary wick can be made from a variety of porous or capillary materials and preferably has a known, pre-defined capillarity. Examples include ceramic- or graphite-based materials in the form of fibers or sintered powders. Wicks of different porosities can be used to accommodate different liquid physical properties such as density, viscosity, surface tension and vapor pressure. The wick must be suitable so that the required amount of liquid can be delivered to the heating coil.

The mouthpiece and shell are sized and shaped so as to engage with one another, so as to produce a suitably sized electrically heated smoking system which can be used by a smoker. The components of the mouthpiece and shell, including the power supply, circuitry, liquid storage portion, wick, heating element and aerosol forming chamber are appropriately sized and shaped for the system design. The system is preferably portable and may have a size similar to that of a conventional cigar or cigarette.

The system of the invention allows the control of particle concentration (milligrams per liter, mg/l or milligrams per puff volume, mg/puff volume) in the aerosol, the average particle size in the aerosol and the distribution (range) of particle sizes in the aerosol. These may be controlled by varying one or more of: the aerosol former formulation in the liquid, the energy transfer (thermal power per unit of surface area) at the heating element, the design of the aerosol forming chamber and the operating temperature. The energy transfer will depend on a number of factors including the materials used for the heating element and the wick, the diameter of the wick, the design of the heating element including, if the heating element is a coil, the length, diameter and pitch (distance between spirals) of the coil, and the power applied to the heating element.

The operating temperature should be controlled to ensure that, as far as possible, no undesirable degradations of the aerosol former or formers and the flavouring material occur. This can be achieved, for example, by controlling the temperature of the heater if the heater is made from a suitable metal or alloy, using the variation in conductivity, or by controlling the amount of energy delivered to the heater. A preferred operating temperature at the heating element is in the range of about 100° to about 300° Celsius. The arrangement shown in the Figures can operate within this temperature range, and may also provide a rapid response time (time between the user puffing on the system and the aerosol entering the user's mouth from the air outlet—this may be referred to as "time to puff") of between about 10 and about 500 milliseconds, ms.

The word "about" is sometimes used in connection with numerical values to avoid an interpretation of those numerical values based on mathematical precision. Accordingly, when the word "about" is used with a numerical value that numerical value should be interpreted to include a tolerance of ±10% around the numerical value.

It is expressly intended that the various parts of this specification be interpreted consistently with one another so as to preserve the full and fair breadth of the claimed invention, and not in a way to restrict that interpretation.

It will now be apparent to those skilled in the art that a new, useful, and nonobvious electrically heated smoking system has been described. Moreover, it will be apparent to those skilled in the art that numerous modifications, variations, substitutions, and equivalents exist for various features of the invention. Accordingly, it is expressly intended that all such modifications, variations, substitutions, and equivalents that fall within the spirit and scope of the appended claims are embraced thereby.

What is claimed is:

1. A vapor generating system comprising:
a mouthpiece housing including an air outlet at a first side of the mouthpiece housing;
a liquid storage portion containing a liquid, the liquid storage portion coupled to the mouthpiece housing and extending outwardly from a second side of the mouthpiece housing, the first side of the mouthpiece housing and the second side of the mouthpiece housing are opposing sides of the mouthpiece housing, the liquid storage portion being made from a plastic, the liquid storage portion not having any porous materials to contain the liquid;
an elongated filamentary wick including a first portion and a second portion, the first portion extending into the liquid storage portion;
a heating coil at least partially surrounding the second portion of the elongated filamentary wick along a length of the elongated filamentary wick, the elongated filamentary wick configured to transfer the liquid from the liquid storage portion to the second portion of the elongated filamentary wick, and the heating coil configured to heat the liquid transferred to the second portion of the elongated filamentary wick and form a vapor, the elongated filamentary wick being only capillary mechanism in the system to transfer the liquid, the second portion of the elongated filamentary wick being substantially linear where the heating coil surrounds the second portion of the elongated filamentary wick, the mouthpiece housing, the liquid storage portion, the elongated filamentary wick and the heating coil being parts of a single replaceable assembly, a portion of which is configured to be inserted into a shell comprising a battery configured to provide power to the heating coil;
an air inlet configured to allow air to flow into the mouthpiece housing, the air inlet upstream of the heating coil along an air flow path, the air outlet in communication with the air inlet;
a chamber between the heating coil and the air outlet along the air flow path, the chamber downstream of the heating coil along the air flow path, the chamber arranged to receive the formed vapor and guide the formed vapor to the air outlet;
the battery configured to provide the power to the heating coil;
a sensor configured to detect airflow; and
a puff indicator configured to operate based on an output of the sensor.

2. The vapor generating system of claim 1, wherein the puff indicator is configured to indicate when the heating coil is activated.

3. The vapor generating system of claim 1, wherein the battery is rechargeable.

4. The vapor generating system of claim 1, wherein the battery is a lithium-ion battery.

5. The vapor generating system of claim 1, wherein the battery is a lithium-ion polymer battery.

6. The vapor generating system of claim 1, wherein the heating coil includes a wire that is formed of a metal alloy.

7. The vapor generating system of claim 1, further comprising:
a cap positioned about the second portion of the filamentary wick, the cap configured to protect the second portion of the filamentary wick.

8. A system comprising:
an assembly including
a mouthpiece housing including an air outlet,
a liquid storage portion containing a liquid, the liquid storage portion coupled to the mouthpiece housing and extending outwardly from a first side of the mouthpiece housing, the liquid storage portion being made from a plastic, the liquid storage portion not having any porous materials to contain the liquid,
an elongated filamentary wick including a first portion and a second portion, the first portion extending into the liquid storage portion,
a heating coil at least partially surrounding the second portion of the elongated filamentary wick along a length of the elongated filamentary wick, the elongated filamentary wick configured to transfer the liquid from the liquid storage portion to the second portion of the elongated filamentary wick, and the heating coil configured to heat the liquid transferred to the second portion of the elongated filamentary wick and form a vapor, the second portion of the elongated filamentary wick being substantially linear where the heating coil surrounds the second portion of the elongated filamentary wick, the elongated filamentary wick being the only capillary mechanism in the system to transfer the liquid, and the mouthpiece housing, the liquid storage portion, the elongated filamentary wick and the heating coil being parts of a single replaceable assembly, a portion of which is configured to be inserted into a shell,
and
a chamber in communication with the air outlet, the chamber between the heating coil and the air outlet; and
the shell including
a battery configured to provide power to the heating coil,
a sensor configured to detect airflow, and
a puff indicator configured to operate based on an output of the sensor, wherein
the chamber is arranged to receive the formed vapor and guide the formed vapor to the air outlet.

9. The system of claim 8, further comprising:
a locking mechanism configured to releasably connect the shell and the assembly.

10. The system of claim 8, further comprising:
at least one air inlet along at least one of the shell and the assembly.

11. The system of claim 8, wherein the heating coil is formed from a metal alloy wire.

12. The system of claim 8, further comprising:
electric circuitry in the shell, the electric circuitry being programmable.

13. The system of claim 8, wherein the shell and the assembly are detachable.

14. The system of claim 8, wherein the battery is rechargeable.

15. The system of claim 8, wherein the battery is a lithium-ion battery.

16. The system of claim 8, wherein the battery is a lithium-ion polymer battery.

* * * * *